United States Patent
Li et al.

(10) Patent No.: US 10,851,060 B2
(45) Date of Patent: *Dec. 1, 2020

(54) METHOD FOR PREPARING 2,6-DICHLOROPYRIDINE THROUGH LIQUID PHASE PHOTOCHLORINATION OF PYRIDINE

(71) Applicant: Zhejiang Avilive Chemical Co., Ltd., Zhejiang (CN)

(72) Inventors: Huiyue Li, Zhejiang (CN); Keqiang Jin, Zhejiang (CN); Jiaquan Zhu, Zhejiang (CN)

(73) Assignee: Zhejiang Avilive Chemical Co., Ltd., Dongyang (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/221,600

(22) Filed: Dec. 17, 2018

(65) Prior Publication Data

US 2020/0131128 A1 Apr. 30, 2020

(51) Int. Cl.
*C07D 213/04* (2006.01)
*C07D 213/61* (2006.01)
*B01D 3/14* (2006.01)
*B01J 19/12* (2006.01)
*C07B 39/00* (2006.01)

(52) U.S. Cl.
CPC ........... *C07D 213/61* (2013.01); *B01D 3/143* (2013.01); *B01J 19/123* (2013.01); *B01J 2219/00033* (2013.01); *B01J 2219/00051* (2013.01); *B01J 2219/0869* (2013.01); *B01J 2219/0884* (2013.01); *C07B 39/00* (2013.01)

(58) Field of Classification Search
CPC .................................................. C07D 213/04
USPC ........................................................ 546/345
See application file for complete search history.

(56) References Cited

FOREIGN PATENT DOCUMENTS

JP 50-154267 A * 12/1975 ........... C07D 213/61

* cited by examiner

*Primary Examiner* — Charanjit Aulakh

(57) ABSTRACT

The present invention relates to a method for preparing 2,6-dichloropyridine with product purity greater than or equal to 99.0% by using trifluoromethyl chlorobenzene as a solvent for reaction between pyridine and chlorine gas. The preparation process comprises the following steps: enabling pyridine and chlorine gas to continuously experience chlorination reaction under irradiation of ultraviolet light by using pyridine and chlorine gas as starting materials and using trifluoromethyl chlorobenzene as a solvent, and cooling a chlorination reaction product and the solvent to obtain pyridine chlorination solution. Advantages: firstly, it pioneers the precedent of direct and high-selectivity preparation of 2,6-dichloropyridine through liquid phase photochlorination, and not only can the 2,6-dichloropyridine product with purity greater than or equal to 99.0% be obtained, but also industrial production is facilitated; and secondly, not only can the reuse of the separated solvent in the preparation process of the 2,6-dichloropyridine product with purity greater than or equal to 99.0% be realized, but also the purposes of low pollution, low energy consumption and low cost in the preparation process can be realized.

9 Claims, No Drawings

METHOD FOR PREPARING 2,6-DICHLOROPYRIDINE THROUGH LIQUID PHASE PHOTOCHLORINATION OF PYRIDINE

TECHNICAL FIELD

The present invention relates to a method for preparing 2,6-dichloropyridine with product purity greater than or equal to 99.0% by using trifluoromethyl chlorobenzene as a solvent for reaction between pyridine and chlorine gas.

BACKGROUND ART

At current, main synthetic methods of 2,6-dichloropyridine include: a gas phase photochlorination method of pyridine aqueous solution, in which an obtained main product is mixture of 2-chloropyridine and 2,6-dichloropyridine, the proportion of 2,6-dichloropyridine is generally 5%-50%, chlorination materials need to be subjected to a series of steps, such as alkali neutralization, crude distillation and rectification, to separate and purify 2,6-dichloropyridine, a great amount of wastewater and waste salt are produced, and the treatment cost of three wastes is high;

an ultraviolet-light-free direct-heating chlorination method of pyridine, in which the yield of 2,6-dichloropyridine is smaller than 30%, the coking rate is about 45%, a great amount of tar is produced and the treatment cost is high;

a liquid phase photochlorination method of 2-chloropyridine, in which the conversion rate of 2-chloropyridine is about 96% within 10 h and the yield of 2,6-dichloropyridine is about 93%, but there are some disadvantages such as blockage of tail gas pipeline by materials, the production process of the raw material 2-chloropyridine also causes the production of a great amount of wastewater and waste salt, and consequently the production cost is high.

SUMMARY OF THE INVENTION

Purpose of design: in order to avoid the shortcomings mentioned in the background art, a method for preparing 2,6-dichloropyridine through liquid phase photochlorination of pyridine, with the purity of the prepared 2,6-dichloropyridine product being greater than or equal to 99.0%, by using trifluoromethyl chlorobenzene as a solvent for reaction between pyridine and chlorine gas, is designed, which overcomes the disadvantages such as that a great amount of three wastes are produced and the materials block the tail gas pipeline in the preparation methods mentioned in the background art, reduces the emission of three wastes, decreases the production cost, facilitates the industrial production, and realizes the low pollution, low energy consumption and low cost in preparation of 2,6-dichloropyridine with purity greater than or equal to 99.0%.

Use of design of the present invention: 2,6-dichloropyridine is an important chemical raw material, from which a variety of fine chemical products can be produced, and which is widely used in the fields of medicine, daily chemical industry, new insecticidal pesticides, etc. Secondly, 2,6-dichloropyridine is a main raw material for producing 2,3,5,6-tetrachloropyridine, sodium trichloropyridinol and 2,3-dichloropyridine, while sodium trichloropyridinol is a key intermediate for producing insecticide chlorpyrifos and weedicide chlorochlorpyridine, and 2,3-dichloropyridine is a key intermediate for producing new insecticide chlorantraniliprole.

In order to realize the purpose of design of the present invention, the present invention designs a method for preparing a 2,6-dichloropyridine product with purity greater than or equal to 99.0% through liquid phase photochlorination reaction at temperature of 150-210° C. under irradiation of ultraviolet light, by using pyridine and chlorine gas as starting materials, using trifluoromethyl chlorobenzene and the like as a solvent, and dripping pyridine and the solvent, which is a main technical feature of the present invention. The purpose of such design is as follow: because reaction materials of the previous batch are reserved in a photochlorination reactor, according to the condition of the heating temperature that the reaction materials can withstand, heating is performed to increase temperature to 150-210° C., and thus not only can the situations of low reaction temperature and slow reaction speed be avoided, but also the situations of high reaction temperature and easy coking and carbonization of materials can be avoided. In the process of liquid phase photochlorination reaction, an ultraviolet light lamp in the chlorination reactor is turned on, chlorine gas is fed into the photochlorination reactor, at the same time pyridine and trifluoromethyl chlorobenzene are mixed according to proportions, and then the mixture is pumped into the photochlorination reactor to continuously experience liquid phase photochlorination reaction under irradiation of light. Since when the photochlorination reactor is firstly started up, it is added with a solvent with a volume greater than 60% of the volume of the photochlorination reactor, as a diluent of the reaction materials, not only does the solvent slow down the intensity of the reaction and reduce the production rate of reaction heat, but also the vaporization of the solvent takes away a great amount of reaction heat, coking of materials caused by excessive local temperature of the reaction material is avoided, more importantly, not only can the yield be improved, but also the preparation efficiency of the 2,6-dichloropyridine product with purity greater than or equal to 99.0% is enabled to be more scientific and simple, the intermediate link in the background art is avoided, and unexpected technical effects are achieved, which are specifically reflected as follows:

Comparative test data of processes for preparing 2,6-dichloropyridine through liquid phase photochlorination of pyridine

| Test comparison item | Preparation method | Coking rate | Yield of 2,6-dichloropyridine | Amount of produced wastewater and waste salt | Treatment cost of three wastes |
|---|---|---|---|---|---|
| Background art | Gas phase photochlorination + liquid phase | 15% | 68.4% | 2.4t (salt)/t | 2700 Yuan/t |

Comparative test data of processes for preparing 2,6-dichloropyridine through liquid phase photochlorination of pyridine

| Test comparison item | Preparation method | Coking rate | Yield of 2,6-dichloropyridine | Amount of produced wastewater and waste salt | Treatment cost of three wastes |
|---|---|---|---|---|---|
| Background art | photochlorination Liquid phase thermal chlorination | 45% | 50% | 1t (tar)/t | 3000 Yuan/t |
| Present invention | Liquid phase photochlorination | 15% | 83.7% | 1.6t (HCl)/t | 250 Yuan/t |

Technical solution: a method for preparing 2,6-dichloropyridine through liquid phase photochlorination of pyridine, wherein pyridine and chlorine gas are enabled to continuously experience chlorination reaction at temperature of 150-210° C. under irradiation of ultraviolet light by using pyridine and chlorine gas as starting materials and using trifluoromethyl chlorobenzene as a solvent, and a chlorination reaction product and the solvent are cooled to obtain pyridine chlorination solution.

Compared with the background art, the present invention firstly pioneers the precedent of direct and high-selectivity preparation of 2,6-dichloropyridine through liquid phase photochlorination, and not only can the 2,6-dichloropyridine product with purity greater than or equal to 99.0% be obtained, but also industrial production is facilitated; and secondly, not only can the reuse of the separated solvent in the preparation process of the 2,6-dichloropyridine product with purity greater than or equal to 99.0% be realized, but also the purposes of low pollution, low energy consumption and low cost in the preparation process can be realized.

DESCRIPTION OF THE EMBODIMENTS

Embodiment 1: a method for preparing 2,6-dichloropyridine through liquid phase photochlorination of pyridine, in which pyridine and chlorine gas were enabled to continuously experience chlorination reaction at temperature of 150-210° C. under irradiation of ultraviolet light by using pyridine and chlorine gas as starting materials and using trifluoromethyl chlorobenzene as a solvent, and a chlorination reaction product and the solvent were cooled to obtain pyridine chlorination solution, i.e., feeding was continuously performed to perform liquid phase chlorination reaction at temperature of 150-210° C. under irradiation of ultraviolet light by using pyridine and chlorine gas as starting materials and using trifluoromethyl chlorobenzene as a solvent to obtain pyridine chlorination solution.

In this embodiment, the weight ratio of pyridine to the solvent is 1:0.2-4. At the start of chlorination reaction, a certain amount of solvent was added into a chlorination reactor in advance, heating was performed to increase temperature to above 150° C., then chlorine gas was continuously fed, at the same time the mixture of pyridine and the solvent is continuously dripped according to proportions, and the reaction solution was continuously discharged into a chlorination material collector or crude distillation kettle. At the start of chlorination reaction, the amount of the added solvent was 10%-80% of the volume of the reactor, and the amount of fed chlorine gas was 1.8-2.5 times the weight of pyridine. The ultraviolet light for irradiation came from an ultraviolet light source or blue light source with a wavelength of 254-400 nm. The solvent included, but not limited to, trifluoromethyl monochlorobenzene, trifluoromethyl dichlorobenzene and trifluoromethyl trichlorobenzene.

Test data of conditions (chlorination materials) for preparing 2,6-dichloropyridine through liquid phase photochlorination of pyridine

| | Reaction temperature (° C.) | | | |
|---|---|---|---|---|
| | 150° C.° C. | 175° C. | 195° C. | 205° C. |
| Weight of chlorination solution (g) | 2788.97 | 2832.30 | 2835.03 | 2836.87 |
| Content of solvent (%) | 57.35 | 56.45 | 56.39 | 56.35 |
| Content of 2,6-clichloropyricline (%) | 36.19 | 39.39 | 39.82 | 38.39 |

Embodiment 2: on the basis of embodiment 1, pyridine and chlorine gas were enabled to continuously experience chlorination reaction at temperature of 150-210° C. under irradiation of ultraviolet light by using pyridine and chlorine gas as starting materials and using heated trifluoromethyl chlorobenzene as a solvent, a chlorination reaction product and the solvent were cooled to obtain pyridine chlorination solution, the chlorination solution was subjected to crude distillation, then tar and high-boiling-point substances were separated, and the obtained distillate was pyridine chloride containing the solvent.

Test data of conditions (crude distillation materials) for preparing 2,6-dichloropyridine through liquid phase photochlorination of pyridine

| | Reaction temperature (° C.) | | | |
|---|---|---|---|---|
| | 150° C. | 175° C. | 195° C. | 205° C. |
| Weight of crude distillate (g) | 2565.42 | 2594.14 | 2596.58 | 2585.93 |
| Content of solvent (%) | 59.21 | 58.59 | 58.56 | 58.66 |
| Content of 2,6-clichloropyridine (%) | 39.33 | 43.84 | 44.02 | 43.09 |
| Weight of tar (g) | 87.47 | 103.73 | 104.93 | 111.68 |
| Coking rate (%) | 12.32 | 14.61 | 14.78 | 15.73 |

Embodiment 3: on the basis of embodiment 1 and embodiment 2, pyridine and chlorine gas were enabled to continuously experience chlorination reaction at temperature of 150-210° C. under irradiation of ultraviolet light by using pyridine and chlorine gas as starting materials and using trifluoromethyl chlorobenzene as a solvent, a chlorination reaction product and the solvent were cooled to obtain pyridine chlorination solution, the chlorination solution was subjected to crude distillation, then tar and high-boiling-point substances were separated, the obtained distillate was pyridine chloride containing the solvent, the content of 2,6-dichloropyridine in the pyridine chloride after the solvent was removed was greater than or equal to 65%, and the pyridine chloride containing the solvent was purified by adopting a rectification method to obtain a 2,6-dichloropyridine product with purity greater than or equal to 99.0%.

Test data of 2,6-dichloropyridine prepared through liquid phase photochlorination of pyridine (rectification separation)

| | Reaction temperature (° C.) | | | |
|---|---|---|---|---|
| | 150° C. | 175° C. | 195° C. | 205° C. |
| Weight of product (g) | 995.49 | 1106.62 | 1121.70 | 1090.86 |
| Content of product (%) | 99.01 | 99.03 | 99.12 | 99.00 |
| Yield of product (%) | 74.2 | 82.5 | 83.7 | 81.3 |

The rectification purification method was to separate and purify 2,6-dichloropyridine from pyridine chloride containing the solvent to obtain the product with purity greater than or equal to 99.0% and the solvent with purity greater than or equal to 95.0%, wherein the solvent was reused.

Embodiment 4: on the basis of embodiment 1 and embodiment 2, pyridine chloride containing the solvent was subjected to separation through cooling crystallization and then the solvent was removed to obtain a 2,6-dichloropyridine product with purity greater than or equal to 99.0%. The crystallization separation purification method was to separate pyridine chloride containing the solvent through cooling crystallization, and to perform rectification to remove the solvent to obtain the 2,6-dichloropyridine product with purity greater than or equal to 99.0% and the solvent with purity greater than or equal to 95.0%, wherein the solvent was reused; and the solvent and part of the product were recovered from the crystallization mother solution through a rectification method.

Test data of 2,6-dichloropyridine prepared through liquid phase photochlorination of pyridine (crystallization separation)

| | Reaction temperature (° C.) | | | |
|---|---|---|---|---|
| | 150° C. | 175° C. | 195° C. | 205° C. |
| Weight of product (g) | 975.58 | 1084.49 | 1099.27 | 1069.04 |
| Content of product (%) | 99.41 | 99.36 | 99.44 | 99.73 |
| Yield of product (%) | 73.01 | 81.12 | 82.29 | 80.26 |

Embodiment 5: the liquid phase photochlorination method in the above-mentioned embodiments may also be implemented intermittently.

Description will be made through examples:

Example 1

1. 80 g (about 50 ml) of trifluoromethyl trichlorobenzene was added as a base material into a 500 ml overflow flask, temperature was increased to 140° C., then chlorine gas was fed at 150 ml/min, an ultraviolet light lamp was turned on, and temperature was continuously increased to 150° C.

2. After temperature was increased to 150° C., 30% pyridine trifluoromethyl trichlorobenzene solution was dripped, the dripping speed was controlled to be 0.5 ml/min, then the temperature was increased gradually with reaction, and finally the reaction temperature was controlled to be 150-210° C.

3. After the reaction solution rose to an overflow opening, the reaction solution began to flow out to a 2000 ml collection bottle, and pyridine was continuously dripped until the raw material solution (710 g of pyridine and 1576 g of trifluoromethyl trichlorobenzene) was fully dripped.

4. After reaction was completed, reduced pressure distillation was performed to the taken-out reaction solution until no distillate was evaporated obviously. The residual solution was tar and weighed.

5. The evaporated distillate was heated and melted, then temperature was slowly decreased to below 10° C. under stirring, then stirring at heat preservation was continuously performed for 1 h below 10° C. until the product was fully precipitated, and then filtration was performed.

6. Filter cake rectification was performed to remove the solvent to obtain the 2,6-dichloropyridine product with purity greater than or equal to 99.0%. The filtrate was directly applied to the next-batch reaction.

Test data of 2,6-dichloropyridine prepared through liquid phase photochlorination of pyridine (different temperature)

| | Reaction temperature (° C.) | | | |
|---|---|---|---|---|
| | 150° C. | 175° C. | 195° C. | 205° C. |
| Weight of product (g) | 975.58 | 1084.49 | 1099.27 | 1069.04 |
| Content of product (%) | 99.41 | 99.36 | 99.44 | 99.73 |
| Coking rate (%) | 12.32 | 14.61 | 14.78 | 15.73 |
| Yield of product (%) | 73.01 | 81.12 | 82.29 | 80.26 |

Example 2

1. 80 g (about 50 ml) of trifluoromethyl trichlorobenzene was added as a base material into a 500 ml overflow flask, temperature was increased to 140° C., then chlorine gas was fed at 110-180 ml/min, an ultraviolet light lamp was turned on, and temperature was continuously increased to 150° C.

2. After temperature was increased to 150° C., 30% pyridine trifluoromethyl trichlorobenzene solution was dripped, the dripping speed was controlled to be 0.5 ml/min, then the temperature was increased gradually with reaction, and finally the reaction temperature was controlled to be 195° C.

3. After the reaction solution rose to an overflow opening, the reaction solution began to flow out to a 2000 ml collection bottle, and pyridine was continuously dripped until the raw material solution (710 g of pyridine and 1576 g of trifluoromethyl trichlorobenzene) was fully dripped.

4. After reaction was completed, reduced pressure distillation was performed to the taken-out reaction solution until no distillate was evaporated obviously. The residual solution was tar and weighed.

5. Rectification was performed to crude distillate to remove the solvent and other components to obtain a 2,6-dichloropyridine product with purity greater than or equal to 99.0%.

Test data of 2,6-dichloropyridine prepared through liquid phase photochlorination of pyridine (different chlorine gas amounts)

| | Chlorine gas speed (ml/min) | | | | |
|---|---|---|---|---|---|
| | 110 | 130 | 150 | 165 | 180 |
| Weight of product (g) | 794.01 | 1093.54 | 1121.83 | 1127.46 | 1119.94 |
| Content of product (%) | 99.09 | 99.17 | 99.12 | 99.05 | 99.11 |
| Coking rate (%) | 18.52 | 15.44 | 14.78 | 12.13 | 12.37 |
| Yield of product (%) | 59.23 | 81.64 | 83.71 | 84.07 | 83.56 |

Example 3

1. 80 g (about 50 ml) of trifluoromethyl trichlorobenzene was added as a base material into a 500 ml overflow flask, temperature was increased to 140° C., then chlorine gas was fed at 150 ml/min, an ultraviolet light lamp was turned on, and temperature was continuously increased to 150° C.

2. After temperature was increased to 150° C., 20-85% pyridine trifluoromethyl trichlorobenzene solution was dripped, the dripping speed was controlled to be 0.72-0.23 ml/min, then the temperature was increased gradually with reaction, and finally the reaction temperature was controlled to be 195° C.

3. After the reaction solution rose to an overflow opening, the reaction solution began to flow out to a 2000 ml collection bottle, and pyridine was continuously dripped until the raw material solution (710 g of pyridine and 2760-126 g of trifluoromethyl trichlorobenzene) was fully dripped.

Other operation steps are the same as those in example 2.

Test data of 2,6-dichloropyridine prepared through liquid phase photochlorination of pyridine (different pyridine concentrations)

| | Pyridine concentration (%) | | | | |
|---|---|---|---|---|---|
| | 20 | 30 | 50 | 65 | 85 |
| Weight of product (g) | 1134.03 | 1121.83 | 1094.91 | 1016.93 | 944.70 |
| Content of product (%) | 99.05 | 99.12 | 99.07 | 99.13 | 99.06 |
| Coking rate (%) | 10.02 | 14.78 | 14.78 | 17.23 | 25.19 |
| Yield of product (%) | 84.56 | 83.71 | 81.66 | 75.89 | 70.45 |

It needs to be understood that, although the above-mentioned embodiments give more detailed descriptions of the design concept of the present invention, these descriptions are only simple descriptions of the design concept of the present invention, instead of limitations to the design concept of the present invention, and any combination, addition or modification that does not go beyond the design concept of the present invention shall fall within the protection scope of the present invention.

What is claimed is:

1. A method for preparing 2,6-dichloropyridine through liquid phase photochlorination of pyridine, wherein pyridine and chlorine gas are enabled to continuously experience chlorination reaction at temperature of 150-210° C. under irradiation of ultraviolet light by using pyridine and chlorine gas as starting materials and using trifluoromethyl chlorobenzene as a solvent, and a chlorination reaction product and the solvent are cooled to obtain pyridine chlorination solution.

2. The method for preparing 2,6-dichloropyridine through liquid phase photochlorination of pyridine according to claim 1, wherein pyridine and chlorine gas are enabled to continuously experience chlorination reaction at temperature of 150-210° C. under irradiation of ultraviolet light by using pyridine and chlorine gas as starting materials and using trifluoromethyl chlorobenzene as a solvent, a chlorination reaction product and the solvent are cooled to obtain pyridine chlorination solution, the chlorination solution is subjected to crude distillation, then tar and high-boiling-point substances are separated, the obtained distillate is pyridine chloride containing the solvent, and the content of 2,6-dichloropyridine in the pyridine chloride after the solvent is removed is greater than or equal to 65%.

3. The method for preparing 2,6-dichloropyridine through liquid phase photochlorination of pyridine according to claim 1, wherein pyridine and chlorine gas are enabled to continuously experience chlorination reaction at temperature of 150-210° C. under irradiation of ultraviolet light by using pyridine and chlorine gas as starting materials and using trifluoromethyl chlorobenzene as a solvent, a chlorination reaction product and the solvent are cooled to obtain pyridine chlorination solution, the chlorination solution is subjected to crude distillation, then tar and high-boiling-point substances are separated, the obtained distillate is pyridine chloride containing the solvent, the content of 2,6-dichloropyridine in the pyridine chloride after the solvent is removed is greater than or equal to 65%, the pyridine chloride containing the solvent is separated by adopting cooling crystallization, the solvent is removed, and then 2,6-dichloropyridine with purity greater than or equal to 99.0% is obtained, or the pyridine chloride containing the solvent is purified by adopting a rectification method to obtain a 2,6-dichloropyridine product with purity greater than or equal to 99.0%.

4. The method for preparing 2,6-dichloropyridine through liquid phase photochlorination of pyridine according to claim 1, wherein pyridine, trifluoromethyl chlorobenzene and chlorine gas are simultaneously and continuously fed into a photochlorination reactor for continuous chlorination reaction.

5. The method for preparing 2,6-dichloropyridine through liquid phase photochlorination of pyridine according to claim 4, wherein, at the start of chlorination reaction, the amount of the added solvent is 60%-80% of the volume of the reactor, heating is performed to increase temperature to above 150° C., then chlorine gas is continuously fed, the amount of fed chlorine gas is 1.8-2.7 times the weight of pyridine, at the same time the mixture of pyridine and the solvent is continuously dripped according to proportions, and reaction solution is continuously discharged into a chlorination material collector or a crude distillation kettle.

6. The method for preparing 2,6-dichloropyridine through liquid phase photochlorination of pyridine according to claim 1, wherein the weight ratio of pyridine to the solvent is 1:0.2-4.

7. The method for preparing 2,6-dichloropyridine through liquid phase photochlorination of pyridine according to claim 1, wherein the rectification purification method is to separate and purify 2,6-dichloropyridine from pyridine chloride containing the solvent to obtain the product with purity greater than or equal to 99.0% and the solvent with purity greater than or equal to 95.0%, wherein the solvent is reused; and the crystallization separation purification method is to separate pyridine chloride containing the solvent through cooling crystallization, and to perform filter cake rectification to remove the solvent to obtain the 2,6-dichloropyridine product with purity greater than or equal to 99.0% and the solvent with purity greater than or equal to 95.0%, wherein the solvent is reused and filtrate is directly applied to the next-batch reaction, or the solvent and part of the product are recovered through a rectification method.

8. The method for preparing 2,6-dichloropyridine through liquid phase photochlorination of pyridine according to claim 1, wherein the ultraviolet light for irradiation comes from an ultraviolet light source or blue light source with a wavelength of 254-400 nm; and the solvent includes, but not limited to, trifluoromethyl monochlorobenzene, trifluoromethyl dichlorobenzene and trifluoromethyl trichlorobenzene.

9. The method for preparing 2,6-dichloropyridine through liquid phase photochlorination of pyridine according to claim 1, wherein the liquid phase photochlorination method may also be implemented intermittently.

* * * * *